United States Patent [19]

Immel et al.

[11] Patent Number: 5,097,071

[45] Date of Patent: Mar. 17, 1992

[54] SUPPORTED COPPER CATALYST, PROCESS FOR ITS PREPARATION AND PROCESS FOR THE PREPARATION OF N-ALKYLATED AROMATIC AMINES USING THIS COPPER CATALYST

[75] Inventors: Otto Immel; Hans-Helmut Schwarz, both of Krefeld; Rudolf Braden, Odenthal, all of Fed. Rep. of Germany

[73] Assignee: Bayer Aktiengesellschaft, Leverkusen, Fed. Rep. of Germany

[21] Appl. No.: 585,590

[22] Filed: Sep. 20, 1990

Related U.S. Application Data

[62] Division of Ser. No. 433,874, Nov. 9, 1989, abandoned.

[30] Foreign Application Priority Data

Nov. 29, 1988 [DE] Fed. Rep. of Germany ....... 3840194

[51] Int. Cl.$^5$ ............................................. C07C 209/00
[52] U.S. Cl. ................................... 564/401; 564/399; 564/418; 564/420
[58] Field of Search ................. 564/399, 401, 418, 420

[56] References Cited

U.S. PATENT DOCUMENTS

| 2,402,440 | 6/1946 | Owen | 564/420 |
| 2,580,284 | 12/1951 | Deahl et al. | 564/401 |
| 3,538,162 | 11/1970 | Dovell | 564/420 |
| 3,637,820 | 1/1972 | Dodman et al. | 564/420 |
| 3,708,539 | 1/1973 | Fenton | 564/401 |
| 4,183,868 | 1/1980 | Radimerski et al. | 564/399 |

FOREIGN PATENT DOCUMENTS

0146534  9/1983  Japan.
0493339  10/1938  United Kingdom.
1413949  11/1975  United Kingdom.

*Primary Examiner*—Allen J. Robinson
*Assistant Examiner*—P. O'Sullivan
*Attorney, Agent, or Firm*—Sprung Horn Kramer & Woods

[57] ABSTRACT

The novel copper catalyst on an $Al_2O_3$-containing carrier which is impregnated with compounds of manganese and of one or more rare earth metals, having a Cu content of 0.1-5% by weight, a total content of compounds of manganese and of the rare earth metal or metals of 0.05 to 8% by weight, calculated as metals, is described, the weight ratio of rare earth metal(s) to manganese being 5:1-1:5, calculated as metal, and all percentages being relative to the total weight of the catalyst. Such catalyst is prepared by first impregnating the carrier with compounds of manganese and of the rare earth metal or metals, then fixing the copper salt on the impregnated carrier and activating the catalyst in a preferred manner by treatment with $H_2$ at 150° to 350° C. Such a catalyst is suitable, for example, for the N-alkylation of aromatic amines with alkanols, where the aromatic amines can be prepared from the parent nitro compounds in an alkylation reactor with simultaneous addition of $H_2$.

17 Claims, No Drawings

SUPPORTED COPPER CATALYST, PROCESS FOR ITS PREPARATION AND PROCESS FOR THE PREPARATION OF N-ALKYLATED AROMATIC AMINES USING THIS COPPER CATALYST

This is a division of application Ser. No. 07/433,874, filed Nov. 9, 1989, now abandoned.

BACKGROUND OF THE INVENTION

The invention relates to a novel supported copper catalyst, a process for its preparation and a process for the preparation of N-alkylated aromatic amines using this copper catalyst. The amines to be alkylated can be prepared in a preferred manner simultaneously in the alkylation reactor from the parent nitro compounds with simultaneous use of hydrogen.

SUMMARY OF THE INVENTION

A novel copper catalyst on an $Al_2O_3$-containing carrier which is impregnated with compounds of manganese and of one or more rare earth metals, having a Cu content of 0.1–5% by weight, preferably 0.1–3% by weight, particularly preferably 1–3% by weight, a total content of compounds of manganese and of the rare earth metal or metals of 0.05 to 8% by weight, preferably 0.2–5% by weight, calculated as metals, the weight ratio of rare earth metal(s) to manganese being 5:1–1:5, preferably 10:9–1:2, calculated as metal, and all percentages being relative to the total weight of the catalyst, have been found.

DETAILED DESCRIPTION OF THE INVENTION

The catalyst according to the invention are accordingly characterized in that they contain the copper on an $Al_2O_3$-containing carrier impregnated in a special manner, with the result that it displays a specific activity. The catalyst according to the invention can accordingly dispense with catalytically active metals.

A suitable $Al_2O_3$-containing carrier is $\alpha$-$Al_2O_3$, $\gamma$-$Al_2O_3$ or an aluminum spinel. Aluminum spinels are compounds of the formula

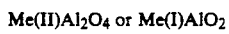

$$Me(II)Al_2O_4 \text{ or } Me(I)AlO_2$$

in which Me(II) is a divalent metal cation of iron, of zinc, of nickel, of copper, of cobalt, of cadmium, of magnesium or other metals, preferably of magnesium, and Me(I) is a monovalent cation, for example lithium (lithium aluminum spinel). The aluminum in the spinels can be partly replaced by trivalent iron, chromium or manganese. $\alpha$- or $\gamma$-$Al_2O_3$ is preferably used, particularly preferably $\gamma$-$Al_2O_3$.

Such a carrier is impregnated with compounds of manganese or of one or more rare earth metals, the above-mentioned amounts and weight ratios being suitable. The following may be mentioned as rare earth metals (subgroup III of the periodic table of elements): scandium, yttrium, lanthanum and the lanthanies. Yttrium, lanthanum, cerium, praseodymium, neodymium and dysprosium are preferred, cerium and lanthanum are particularly preferred and cerium is very particularly preferred. Cerium may be associated with other lanthanides, for example with lanthanum, praseodymium, neodymium, dysprosium or with yttrium. Such an association is familiar to the skilled worker in general for all rare earth metals mentioned.

The catalyst according to the invention is furthermore characterized by the stated content of copper on the impregnated $Al_2O_3$-containing carrier described.

In a preferred variant, the catalyst may furthermore additionally contain 1–6% by weight, preferably 2–5% by weight, relative to the total weight of the catalyst, of alkali metal hydroxide. Alkali metal hydroxides are lithium hydroxide, sodium hydroxide, potassium hydroxide, rubidium hydroxide, caesium hydroxide or a mixture of these, preferably lithium hydroxide, sodium hydroxide, potassium hydroxide or a mixture of these, particularly preferably sodium hydroxide, potassium hydroxide or a mixture of these.

For the preparation of the catalyst, the carrier can be used in pulverulent or lump form.

Where the catalyst according to the invention is used in the fixed-bed process, the lump form is preferred. For example, extrudates, pellets or spheres having dimensions of about 2–10 mm may be mentioned as the lump form.

For the preparation of the catalyst according to the invention, such a carrier is treated with compounds of cerium and of manganese, the carrier treated in this manner, after drying at 200°–450° C., preferably 250° to 430° C., is heated and is then prepared for further treatment with a copper salt, which can be applied by impregnation or spraying on, after which a further drying phase follows. Application of the rare earth metal or metals and of the manganese to the catalyst carrier can be effected, for example, simply by impregnation or spraying with suitable salts of these metals, after which a drying phase and the stated heating phase follow. Drying is carried out in a manner familiar to the skilled worker at 80°–130° C., optionally in a vacuum drying oven. In the subsequent heating phase, the metal salts are converted into compounds which adhere firmly to the catalyst carrier. Application of the stated metals can, however, also be carried out by joint precipitation of a metal hydroxide mixture from salts of the stated metals onto the carrier with the aid of an alkali metal hydroxide solution or ammonia and optionally subsequent washing out of the soluble components with water. Suitable salts of the stated metals are, in particular, the sulfates, chlorides, acetates and/or nitrates.

The subsequent drying and heating in the stated temperature ranges are each carried out in a time of 1–120 hours; during this time, the temperature can be increased from lower to higher values in the stated ranges. After the heating phase (tempering) described, the catalyst carrier impregnated with the stated metal compounds is impregnated with a copper-containing solution. Here, it is possible to adopt a procedure in which the copper, for example in the form of aqueous solutions of the chloride, of the nitrate, of the acetate or of another suitable salt, is applied to the carrier by impregnation or spraying on, followed by drying. However, it is also possible for the copper-impregnated carrier to be treated, before drying, with a solution of the stated basic compounds, the copper being precipitated as the oxide or hydroxide. Here too, this is followed by drying, which can be carried out under the abovementioned conditions.

Thereafter, such a catalyst according to the invention is in principle available for use. Preferably, however, it is activated before it is used, particularly preferably after being arranged in the reactor intended for its use, by treatment with hydrogen at a temperature of 150°–350° C. After the activation, it may be desirable to remove anions such as chloride, nitrate, acetate or other anions and, if appropriate, the cations of the basic compounds used for the precipitation, by means of a water wash, which can also be carried out with the catalyst arranged beforehand in the reactor.

However, it is also possible for the catalyst impregnated with the stated metal compounds first to be impregnated with a solution of one of the stated basic compounds and then dried, and for solutions of copper salts to be applied to the catalyst carrier which has been pretreated in this manner and rendered basic, precipitation of the copper in the form of its oxide or hydroxide also being effected at the time of impregnation. Here, too, the catalyst is in principle ready for use after a final drying, but may preferably be activated beforehand, in the manner described, with hydrogen at the stated temperature.

A catalyst treated with basic compounds to precipitate the copper as the oxide or hydroxide is in principle ready for use in the presence of the residues of such alkaline compounds. The content of such alkaline compounds has already been mentioned above as a preferred embodiment of the catalyst according to the invention.

The impregnation or spraying of the $Al_2O_3$-containing carrier with the stated substances and the apparatus as required for this purpose are known to the skilled worker; the adjustment of the desired treatment by the choice of the amount and concentration of the solutions of the stated metal compounds is also known.

For example, conversion into insoluble oxides and/or hydroxides of copper or a reduction of the copper salt to elemental copper with the hydrogen may be mentioned as methods of fixing the copper to the carrier.

If appropriate, part of the copper may be in the form of the oxides/hydroxides and a further part in the form of a metallic copper.

The catalyst according to the invention is outstandingly suitable for the preparation of secondary and/or tertiary aromatic amines by N-alkylation of aromatic amines with alkanols.

It is known that, for the preparation of N-alkylated aromatic compounds, aromatic amines can be reacted with alkanols or the associated dialkyl ethers in the gas phase. For example, alumina or silicates have been proposed as catalysts (for example silicates, such as tonsil, in German Patent Specification 638,756). The stated catalysts have the disadvantage that their activity rapidly decreases during the alkylation of aromatic amines (cf. Houben-Weyl, Methoden der organischen Chemie (Methods of organic chemistry), volume XI/1 (1957), page 126).

Furthermore, German Patent Specification 617,990 and DE-OS (German Published Specification) 2,335,906 discloses that carriers which contain oxo acids of phosphorus can be used for the stated purpose. The life and selectivity of such catalysts are, however, unsatisfactory for industrial processes.

Furthermore, U.S. Pat. No. 2,580,284 has proposed reacting aniline and methanol using a catalyst which contains metallic copper on $Al_2O_3$ and further oxides, such as zinc oxide, cadmium oxide, iron oxide, chromium oxide, calcium oxide, magnesium oxide or potassium oxide. Such catalysts suffer from the deposition of tar-like substances after a relatively short time.

A further process for the reaction of aniline with methanol to give N-methylaniline according to DE-OS (German Published Specification) 2,061,709 is carried out over a chromium catalyst which can contain copper, zinc, iron, nickel or molybdenum and barium, magnesium or manganese. This process has the disadvantage that it is carried out under a pressure of 50-150 bar and is therefore too expensive for industrial use; furthermore, this catalyst does not have an adequate life.

According to DE-OS (German Published Specification) 2,120,641, copper chromite catalysts with barium, manganese, cerium and others as promoters are used for the preparation of secondary or tertiary aromatic amines from aliphatic alcohols and aromatic nitro compounds. However, this process leads only to unsatisfactory yields.

Among the large number of catalysts investigated to date, it is therefore surprising that the catalyst according to the invention avoids the stated disadvantages with the use of a specially impregnated carrier and while dispensing with chromium as an active catalyst component.

The invention therefore also relates to a process for the preparation of aromatic amines of the formula

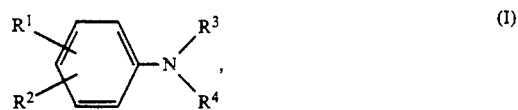

in which
R[1] and R[2] independently of one another denote hydrogen or straight-chain or branched $C_1$-$C_5$-alkyl or $C_1$-$C_5$-alkoxy and together may also denote a fused benzene ring, and
R[3] and R[4] independently of one another represent straight-chain or branched $C_1$-$C_{10}$-alkyl or $C_3$-$C_{10}$-cycloalkyl, and R[4] can additionally represent hydrogen, by catalytic conversion of aromatic amines of the formula

with alkanols of the formula $R^3OH$          (III)

or the associated ethers $R^3$—O—$R^3$, wherein $R^3$ and $R^4$ have the above meaning, which is characterized in that the reaction is carried out at 160°-400° C. in the gas phase in the presence of the catalyst according to the invention as described above, 0.5-20 mol of alkanol per mol of the aromatic amine being employed.

The following may be mentioned as examples of straight-chain or branched $C_1$-$C_5$-alkyl or $C_1$-$C_5$-alkoxy: methyl, ethyl, propyl, isopropyl, butyl, isobutyl, the various amyl radicals, methoxy, ethoxy, propoxy, isopropoxy, butoxy, isobutoxy and the various amyloxy radicals. Methyl, ethyl, methoxy and ethoxy may be preferably mentioned as such radicals, particularly preferably methyl and methoxy. $C_3$-$C_{10}$-cycloalkyl is, for example, cyclopropyl, cyclobutyl, cyclopentyl, cyclohexyl, cycloheptyl, cyclooctyl, methyl-cyclopentyl, methyl-cyclohexyl, 4-tert-butyl-cyclohexyl, menthyl, preferably cyclopropyl, cyclopentyl and cyclohexyl.

Aromatic amines which are not substituted in the nucleus are very particularly preferably used as starting materials.

Aromatic amines of the formula

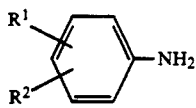

(IV)

wherein $R^1$ and $R^2$ have the above meaning, are also preferably used as starting materials.

Aromatic amines of the formula

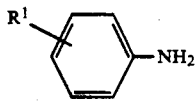

(V)

where $R^1$ has the above meaning, are also preferably used as starting materials.

A list of aromatic amines for the process according to the invention, which is intended by way of example and is no way exhaustive, is the following: aniline, 1-naphthylamine, o-, m- and p-toluidine, o-, m-and p-ethylaniline, the isomeric xylidines, such as 2,3-, 2,4-, 2,5-, 2,6-, 3,4- or 3,5-dimethylaniline, and 4-methyl-1-naphthylamine.

The process according to the invention is carried out in the gas phase at a temperature of 160°–400° C., preferably 160°–350° C., a pressure of 0.5–10 bar, preferably 0.5 to 3 bar, and a catalyst space velocity of 0.1–2 kg of starting material per liter of catalyst per hour. The catalyst space velocity and the residence time arising therefrom are inversely proportional to one another in a known manner.

The aromatic amine used as starting material is vaporized before entering the reaction space and is passed over the catalyst arranged as a fixed bed. In a preferred procedure, the vaporized starting material is diluted with a carrier gas stream, for example with $H_2$, $N_2$, $H_2O$ vapour, $CH_4$ and other inert gases.

Alkanols for the process according to the invention are open-chain alkanols having 1–10 C atoms, preferably having 1–6 C atoms, particularly preferably having 1–2 C atoms, and cyclic alkanols having 3–10 C atoms, preferably having 3, 5 or 6 C atoms, such as methanol, ethanol, propanol, i-propanol, butanol, i-butanol, tert-butanol, pentanol, i-pentanol, the isomeric hexanols, heptanols, octanols or decanols, cyclopropanol, cyclobutanol, cyclopentanol, cyclohexanol, cycloheptanol or cyclooctanol, and 2-, 3- or 4-methyl-cyclohexanol, 2-ethyl-cyclohexanol, 3,3,5-trimethylcyclohexanol, 4-tert-butyl-cyclohexanol and menthol ($C_{10}$).

Instead of the alcohols, it is also possible to use the associated ethers $R^3$—O—$R^3$; however, the use of the alkanols is preferred.

The molar ratio of the alkanol to the aromatic amine to be N-alkylated is 0.5–20:1, preferably 0.7–15:1. When the associated ethers are used, 1 mol of $R^3$—O—$R^3$ should be taken as equivalent to 2 mols of $R^3OH$ for calculating the molar ratio. With such molar amounts of alkanol, tertiary aromatic amines of the formula (I), in which $R^4$ therefore differs from hydrogen, can be prepared from secondary aromatic amines of the formula (II), in which $R^4$ therefore differs from hydrogen. Furthermore, secondary or tertiary amines or a mixture of these, in which the amine N atom is thus monoalkylated or dialkylated, can be prepared from primary aromatic amines of the formula (II), in which $R^4$ represents hydrogen, or from aromatic amines of the formulae (IV) and (V). In the case of only mono-N-alkylation, it is furthermore preferable to use an even narrower molar range of 0.8–5 mol of alkanol per mol of primary aromatic amine. Since the separation of aromatic amines monoalkylated and dialkylated at the N atom is frequently difficult, it is desirable, in the preparation of aromatic amines which are only monoalkylated, to suppress as far as possible the amount of amines dialkylated at the N atom. This desire is fulfilled in a surprisingly good manner by the use of the catalyst according to the invention as described above. Here, it was found, surprisingly, that aromatic amines which are virtually exclusively monoalkylated at the N atom are formed, even with relatively large molar amounts of alkanol, i.e. up to 5 mol per mol of the primary aromatic amine, if the temperature is kept in the lower temperature range and the residence times are kept in the lower range of the residence times. For example, the following may be mentioned for this purpose: 160°–220° C. and residence times of 0.5 to 8 sec.

Conversely, higher reaction temperatures and longer residence times, for example 230°–300° C. and 5 to 20 sec, in conjunction with higher molar excesses of alkanol in the stated range lead to virtually exclusive dialkylation at the N atom.

In a preferred variant of the process according to the invention, the starting materials used are not aromatic amines of the formula (IV) but the parent aromatic nitro compounds of the formula

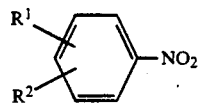

(VI)

wherein $R^1$ and $R^2$ have the above range of meanings.

In this case, at least the amount of hydrogen required for the reduction of the nitro group to the amino group should be additionally used, the hydrogen also serving as a carrier gas stream in this case too. Preferably, however, excess hydrogen is used and is recycled after being separated off from the reaction product. For example, 150 to 1000% of the stoichiometric amount of hydrogen required for the reduction of the nitro group may be mentioned as such an excess. The abovementioned inert gases can be added to the hydrogen for dilution.

A list of suitable aromatic nitro compounds for the process according to the invention, which list is intended by way of example and is in no way exhaustive, is the following: nitrobenzene, o-, m- and p-methyl-nitrobenzene and o-, m- and p-ethyl-nitrobenzene.

N-alkylated aromatic amines which can be prepared according to the invention are starting materials for the production of dyes, pest-combating agents or other biological active compounds, such as plant protection agents, growth regulating agents, etc. They are also used as mineral oil additives or as additives for coatings and other polymeric systems.

EXAMPLE 1

200 g of a commercial $\gamma$-$Al_2O_3$ having a specific surface area of 350 $m^2/g$ and sphere diameter of 2 to 6 mm was impregnated with a solution which had been prepared from 12.4 g of Ce(NO₃)₃ 6 H₂O, 18.28 g of Mn(NO₃)₂ 4 H₂O and 50 g of water. The impregnated Al₂O₃ was dried in a vacuum from a water jet for 18 hours at 120° C. and then heated for 3 hours at 400° C. The catalyst carrier thus prepared was impregnated with 70 g of an aqueous Cu(NO₃)₂ solution which contains 4 g of Cu. The moist catalyst was dried and was activated for 3 hours in a stream of hydrogen (100 l of H₂O/h) at 350° C. Thereafter, 58.8 g of the catalyst was again impregnated with a solution of 1.2 g of NaOH in 20 g of water and again dried. A further 58.8 g of the activated catalyst was impregnated with a solution of 1.2 of KOH in 20 g of water and likewise again dried.

EXAMPLE 2

20 ml (17.4 g) of the catalyst prepared according to Example 1, which catalyst had been after-treated with KOH, were introduced into a reaction tube which had an internal diameter of 17 mm and a length of 60 mm. The reaction tube was kept at 250° C. by means of an electric heater, while 258 g of a mixture of ethanol and nitrobenzene and 20 l of H₂/h were passed into the reaction tube using a calibrated metering apparatus in the course of 15.5 hours. Ethanol and nitrobenzene were present in the starting mixture in a molar ratio of 4:1. The reaction product was condensed and was analysed by gas chromatography. The water content was not determined; the organic content of the reaction product had the following composition:
nitrobenzene: 0.3%
aniline: 5.7%
N-methylaniline: 90.6%
N,N-dimethylaniline: 3.2%
byproducts: 0.2%

EXAMPLE 3

With the use of the same apparatus and the same amount of catalyst as in Example 2, m-nitrotoluene and ethanol in a molar ratio of 1:4 and 20 l of H₂/h were employed. The reaction temperature was adjusted to 220° C. The catalyst space velocity was 0.81 g of mixture/ml of catalyst per hour. The reaction product formed in the course of 16 hours had the following composition, according to gas chromatography:
m-toluidine: 0.7%
N-ethyl-m-toluidine: 90.6%
N,N-diethyl-m-toluidine: 6.1%
byproducts: 2.6%

EXAMPLE 4

With the use of the same apparatus and the same catalyst as in Examples 2 and 3, aniline and ethanol in a molar ratio of 1:4 were employed. The carrier gas used was hydrogen (20 l/h). At a reaction temperature of 200° C. and a catalyst space velocity of 0.72 g of ethanol/aniline mixture per ml of catalyst per hour, a reaction mixture having the following composition was formed in the course of 63 hours:
aniline: 3.1%
N-ethaneaniline: 95.6%
N,N-diethylaniline: 0.5%
byproducts: 0.8%

EXAMPLE 5

30 ml (25.6 g) of the Cu-Ce-Mn/Al₂O₃/NaOH catalyst prepared according to Example 1 were used for the reaction of nitrobenzene with methanol at 250° C. (as in Example 2). A mixture which contained nitrobenzene and methanol in a molar ratio of 1:4 was used. 20 l of H₂ per hour were passed over the catalyst. The methanol/nitrobenzene mixture used was fed in at a catalyst space velocity of 0.42 g/ml per h. The reaction, which was carried out continuously, gave, in 74 hours, a reaction mixture having the following composition:
aniline: 25.7%
N-methylaniline: 72.5%
N,N-dimethylaniline: 1.6%
byproducts: 0.2%

What is claimed is:

1. A process for the preparation of an aromatic amine of the formula

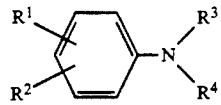

in which
R¹ and R² independently of one another denote hydrogen or straight-chain or branched C₁-C₅-alkyl or C₁-C₅-alkoxy and together may also denote a fused benzene ring, and
R³ and R⁴ independently of one another represent straight-chain or branched C₁-C₁₀-alkyl or C₃-C₁₀-cyclo alkyl, and R⁴ can additionally represent hydrogen, comprising the catalytic reaction of an aromatic amine of the formula

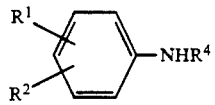

with an alkanol of the formula

R³OH or the associated ethers R³—O—R³, wherein
R³ and R⁴ have the above meaning,
at elevated temperature, wherein the reaction is carried out at 160°–400° C. in the gas phase in the presence of a copper catalyst on an Al₂O₃-containing carrier which is impregnated with compounds of manganese and of one or more rare earth metals, having a Cu content of 0.1-5% by weight, a total content of compounds of manganese and of the rare earth metal or metals of 0.05-8% by weight, calculated as metals, the weight ratio of rare earth metal(s) to manganese being 5:1-1:5, calculated as metal, and all percentages being relative to the total weight of the catalyst, and 0.5-20 mol of alkanol per mol of the aromatic amine being employed.

2. The process of claim 1, wherein the aromatic amine is of the formula

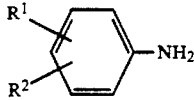

in which

R[1] and R[2] independently of one another denote hydrogen, straight-chain or branched $C_1$-$C_5$-alkyl or $C_1$-$C_5$-alkoxy.

3. The process of claim 2, wherein the aromatic amine is prepared in an alkylation reactor with simultaneous addition of hydrogen from the parent nitro compound of the formula

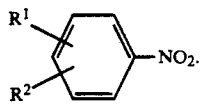

4. The process of claim 1, wherein the gas-phase reaction is carried out under a pressure of 0.5 to 10 bar.

5. The process according to claim 1, wherein in the catalyst the Cu content is 0.1-3% by weight, relative to the total weight of the catalyst.

6. The process of claim 5, wherein the Cu content is 1-3% by weight, relative to the total weight of the catalyst.

7. The process according to claim 1, wherein in the catalyst the total content of compounds of manganese and of the rare earth metal or metals is 0.2%-5% by weight, calculated as metals.

8. The process according to claim 1, wherein in the catalyst the weight ratio of rare earth metal(s) to manganese is 10:9-1:2, calculated as metal.

9. The process according to claim 1, wherein in the catalyst the carrier is $\alpha$-$Al_2O_3$ or $\gamma$-$Al_2O_3$.

10. The process according to claim 1, wherein the the catalyst has an additional content of 1-6% by weight, relative to the total weight of the catalyst, of alkali metal hydroxide.

11. The process of claim 10, wherein the alkali metal hydroxide is lithium hydroxide, sodium hydroxide, potassium hydroxide or a mixture of these.

12. The process of claim 11, wherein the alkali metal hydroxide is sodium hydroxide, potassium hydroxide or a mixture of these.

13. The process according to claim 1, wherein the catalyst is prepared by treatment of the carrier with soluble compounds of manganese and of the rare earth metal or metals, conversion of these compounds into compounds which adhere firmly to the carrier, by drying and subsequent heating at 200°-450° C., impregnation of the heated carrier thus obtained with a soluble copper salt and fixing of the copper on the carrier.

14. The process of claim 13, wherein the subsequent heating is carried out at 250°-430° C.

15. The process of claim 13, wherein after fixing the copper on the carrier a treatment for activation with hydrogen is carried out at 150°-350° C.

16. the process of claim 15, comprising impregnation with 1-6% by weight, relative to the total weight of the catalyst, of one or more alkali metal hydroxides after the activation.

17. The process of claim 15, wherein the activating treatment with hydrogen is not carried out until directly before the catalyst is used in the reactor intended for this purpose.

* * * * *